United States Patent [19]

Idel et al.

[11] 4,137,219

[45] Jan. 30, 1979

[54] POLYCONDENSATES CONTAINING HYDROXYQUINOLINE END GROUPS, THEIR USE FOR THE PREPARATION OF POLYMERS CONTAINING METALS AND METAL CONTAINING POLYCONDENSATES

[75] Inventors: Karsten Idel, Krefeld; Hugo Vernaleken, Krefeld-Bockum; Dieter Freitag, Krefeld, all of Germany; Günther Reiff, Santa Maria, Brazil; Hans Rudolph, Krefeld, Germany

[73] Assignee: Bayer Aktiengesellschaft, Leverkusen, Germany

[21] Appl. No.: 825,506

[22] Filed: Aug. 17, 1977

Related U.S. Application Data

[62] Division of Ser. No. 549,282, Feb. 12, 1975, abandoned.

[30] Foreign Application Priority Data

Feb. 15, 1974 [DE] Fed. Rep. of Germany ....... 2407309

[51] Int. Cl.² ...................... C08G 69/32; C08G 69/42

[52] U.S. Cl. ................................. 528/177; 260/857 R; 528/184; 528/186; 528/187; 528/289; 528/197; 528/201; 528/333; 528/340; 528/341; 521/30

[58] Field of Search .......... 260/47 C Z, 78 R, 465 E, 260/50, 47 XA

[56] References Cited

U.S. PATENT DOCUMENTS

| 3,133,045 | 5/1964 | Deanin et al. | 260/47 |
|---|---|---|---|
| 3,875,112 | 4/1975 | Bockmann et al. | 260/47 |

OTHER PUBLICATIONS

Chemical Abstracts, 46, 206(h) (1952), 57, 722h (1962).

*Primary Examiner*—Lester L. Lee

*Attorney, Agent, or Firm*—Gene Harsh; Lawrence S. Pope

[57] ABSTRACT

The present invention relates to polycondensates of the formula 10, their use for absorbing metal ions of the transition elements of the periodic system and their use for the preparation of polymers containing metals of formula 11 which have e.g. improved resistance to heat and to chemicals compared to the corresponding polycondensates of formula 10.

17 Claims, No Drawings

POLYCONDENSATES CONTAINING HYDROXYQUINOLINE END GROUPS, THEIR USE FOR THE PREPARATION OF POLYMERS CONTAINING METALS AND METAL CONTAINING POLYCONDENSATES

This is a division of application Ser. No. 549,282, filed Feb. 12, 1975, and now abandoned.

The present invention relates to polycondensates of the fomula 10

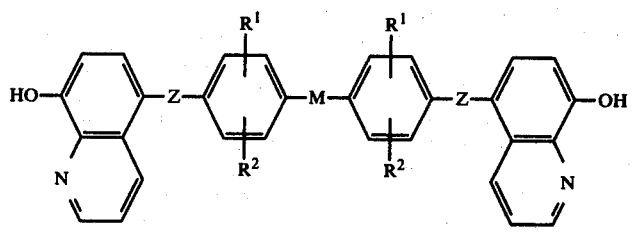

wherein
$R^1$ and $R^2$ are identical or different and denote hydrogen, ($C_1$–$C_4$)-alkyl, phenyl or halogen (for example chlorine or bromine) and
Z is $CH_2$, $CH$—$CH_3$, an isoalkylidene radical with 3 to 5 carbon atoms, a cycloalkylene or cycloalkylidene radical with 5 to 15 carbon atoms, or a radical of the formulae 2

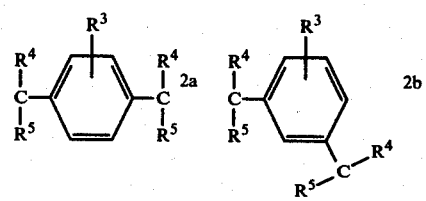

in which
$R^4$, $R^5$ and $R^3$ are identical or different alkyl radicals with 1 to 5 carbon atoms, and
M is a polycarbonate segment, preferably of the formula

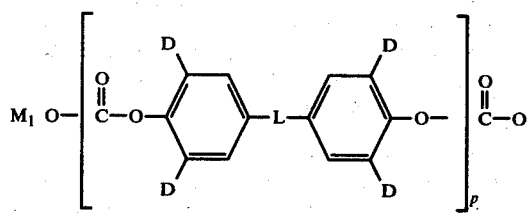

or a polyester segment, preferably of the formula

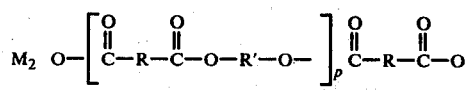

or a polyamide segment, preferably of the formula

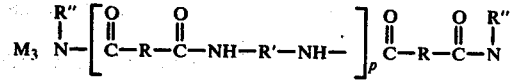

The polycarbonate segments have molecular weights $\overline{M}n$ in the range from 1,000 to 30,000; the polyester segments and the polyamide segments have molecular weights $\overline{M}n$ in the range from 800 to 25,000. ($\overline{M}n$ is determined by membrane osmometry in usual solvents at 20° C.).

In the polycarbonate segments $M_1$
D is chlorine, bromine, hydrogen or $C_1$–$C_4$-alkyl,
L is a single bond, $C_1$–$C_5$-alkylene, $C_2$–$C_5$-alkylidene, $C_5$–$C_{15}$-cycloalkylene, $C_5$–$C_{15}$-cycloalkylidene or a radical of the following formula

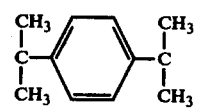

and
p is an integer between 2 and 50;
in the polyester segments $M_2$
R and R' are identical or different and denote $C_2$–$C_{12}$-alkylene which can be interrupted by -O- or cyclohexylene, $C_5$–$C_{15}$-cycloalkylene, $C_8$–$C_{12}$-arylenedialkylene, for example $C_8$–$C_{12}$-phenylenedialkylene, $C_6$–$C_{12}$-arylene, for example phenylene, naphthylene or diphenylene, and $C_{13}$–$C_{15}$-alkylidene-diphenylene and
p denotes an integer between 2 and 50;
in the polyamide segments $M_3$
R'' is hydrogen and $C_1$–$C_4$-alkyl, and
R, R' and p are as defined in $M_2$.

A process for the preparation of the polycondensates according to the invention, containing 8-hydroxyquinoline end groups, of the formula 10 is to co-condense 8-hydroxyquinolines of the formula 1

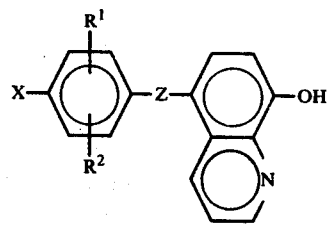

in which
X represents OH or $NH_2$ or NH—($C_1$–$C_4$)-alkyl, $R^1$ and $R^2$ are identical or different and denote hydrogen, ($C_1$-$C_4$)-alkyl, phenyl or halogen (for example chlorine or bromine) and Z denotes $CH_2$, $CH$—$CH_3$, an isoalkylidene radical with 3 to 5 carbon atoms, a cycloalkylene or cycloalkylidene radical with 5 to 15 carbon atoms or a radical of the formulae 2

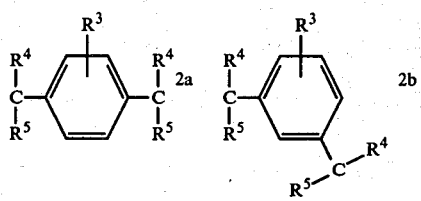

and which are described in German Patent Application No. P 24 07 308 (Le A 15 355) filed on the same day, directly with the starting compounds which are needed to synthesise the polycondensate segments M of the formula 10 in accordance with known processes.

In carrying out this process it was found, surprisingly, that, for example, when preparing polycarbonates with 8-hydroxyquinoline end groups in accordance with the processes customary for polycarbonate syntheses, the functional 8-hydroxyquinolines of the formula 1 (X = OH) added in the condensation reaction are condensed onto the chain end and thus react specifically as chain stoppers, so that the complex-forming centre of the 8-hydroxyquinolyl radical remains preserved.

The action of the functional 8-hydroxyquinolines as chain stoppers was confirmed by means of end group analysis and by comparison of the molecular weights determined in this way with the measured values from independent molecular weight determinations (e.g. determination via viscosity or membrane osmometry).

By controlled addition of the functional 8-hydroxyquinolines of the formula 1, in amounts of 2 mol % to 50 mol % relative to the sum of the remaining starting compounds, as chain stoppers, it is possible to obtain polycondensates, with 8-hydroxyquinoline end groups of the formula 10, of the desired chain length, in which the polymer units p of the polycarbonates, polyesters or polyamides, as defined above for formula 10, can be present two-fold to fifty-fold.

Compounds of the formula 10 are prepared, depending on the nature of the desired polycondensate segments, in accordance with the variants customary for the preparation of polycondensates, the radical X of the functional hydroxyquinolines of the formula 1 being OH for the synthesis of polycarbonates and polyesters and $NH_2$ or NH—($C_1$-$C_4$-alkyl) for the synthesis of polyamides.

A preferred process for the preparation of the polycarbonates with 8-hydroxyquinoline end groups according to the formula 10 (M = $M_1$) is, for example, to react bis-phenol components, together with the functional 8-hydroxyquinolines of the formula 1 (X = OH), under the conditions of a phase boundary reaction, with phosgene or with the bis-chlorocarbonic acid esters of bis-phenol components in a mixture of an aprotic water-immiscible solvent, such as, for example, dichloroethane, methylene chloride, chloroform, monochlorobenzene and dichlorobenzene, and aqueous alkali metal hydroxide solution, in the presence of suitable catalysts, for example triethylamine. At temperatures around 20° C. that is between 0° C. and 40° C., somewhat more than the equimolar amount of phosgene is employed for this reaction.

To control the molecular weight, up to 50 mol %, based on the sum of the remaining starting substances, of the functional 8-hydroxyquinolines of the formula 1 (X = OH) are used as chain stoppers.

The polycarbonates can be worked up in accordance with customary processes such as, for example, by precipitation or by evaporation of the solvent, in which case the phase containing the polycarbonate is preferably first washed until free of electrolyte. (Literature on the preparation of polycarbonates: H. Schnell, Chemistry and Physics of Polycarbonates, Interscience Publishers, London 1964).

Examples of suitable diphenols for the preparation of polycarbonates according to the formula 10 (M = $M_1$) are 4,4'-dihydroxydiphenyl, bis-(4-hydroxyphenyl)-propane-2,2 (bis-phenol A), bis-(4-hydroxy-3,5-dichlorophenyl)-propane-2,2 (tetrachlorobisphenol), bis-(4-hydroxy-3,5-dibromophenyl)-propane-2,2 (tetrabromobisphenol A), bis-(4-hydroxy-3,5-dimethylphenyl)-propane-2,2 (tetramethylbisphenol A), bis-(4-hydroxy-3-methyl-phenyl)-propane-2,2 and bis-(4-hydroxyphenyl)-cyclohexane-1,1 (bisphenol Z). Further diphenols suitable for the preparation of polycarbonates are described in U.S. Pat. Nos. 3,028,365, 2,999,835, 3,148,172, 3,271,368, 2,970,131, 2,991,273, 3,271,367, 3,280,078, 3,014,891 and 2,999,846 and in German Offenlegungsschriften (German Published Specifications) Nos. 2,063,050 (Le A 13 359), 2,063,052 (Le A 13 425), 2,211,957 (Le A 14 240) and 2,211,956 (Le A 14 249).

Several processes are available for the preparation of polyesters with 8-hydroxyquinoline end groups according to the formula 10 (M = $M_2$). A customary process which is preferentially suitable for the preparation of the polyesters from glycols and aromatic dicarboxylic acid esters is the trans-esterification process. In this process, as is known, the dicarboxylic acid esters of readily volatile alcohols, such as, for example, terephthalic acid dimethyl ester, are condensed with appropriate glycols, such as, for example, ethylene glycol, at temperatures of 120°–300° C., optionally using reduced pressure and optionally in the presence of acid or basic catalysts, for example mineral acids or alkali metal alcoholates and alkaline earth metal alcoholates, and with the functional 8-hydroxyquinolines of the formula 1 (X = OH), and the dicarboxylic acid esters can be added in an excess of up to 50 mol %, relative to the glycol component, depending on the desired degree of polymerisation of the polyester.

(Literature on the trans-esterification process: W. H. Carothers and F. J. van Natta, J. Amer. Chem. Soc. 52, 314 (1930); U.S. Pat. No. 2,534,028 (1948), Du Pont, inventor: E. F. Izard).

If polyesters of the formula 10 (M = $M_2$) based on diphenols and aromatic dicarboxylic acids are desired, it is possible to use the process of solution polycondensation with dicarboxylic acid chlorides, for example isophthalic acid dichloride, and bisphenols, for example bisphenol A, as starting compounds, with the reaction with the functional 8-hydroxyquinolines of the formula 1 (X = OH) preferably being carried out by the variant by phase boundary condensation at about 20° C. and the sum of the phenolic components being employed in a slight excess relative to the bifunctional acid chloride. At times it may be advisable to add a wetting agent such as, for example, sodium lauryl-sulphate. Suitable solvents are $CH_2Cl_2$, $CHCl_3$, dichloroethane, monochlorobenzene and dichlorobenzene. In this method, it is an advantage that the reactivity of the functional groups of the 8-hydroxyquinolines according to the formula 1 (X = OH) differs and almost quantitatively only the functional centre X participates in the condensation. (Literature on solution polycondensation: H. Batzer, H. Holtschmidt, F. W. Wiloth and B. Mohr, Makromolekulare Chemie 7, 82 (1951); W. R. Sorenson and T. W. Campbell: Präparative Methoden der Polymeren-Chemie (Preparative Methods in Polymer Chemistry), page 118, Verlag Chemie, Weinheim 1962).

The polyesters of the formula 10 (M = $M_2$) based on aliphatic or cycloaliphatic carboxylic acids and glycols or aliphatic or cycloaliphatic carboxylic acids and diphenols are also obtained according to one of the processes mentioned.

Examples of suitable dicarboxylic acids, or of their esters, anhydrides and chlorides, for the preparation of polyesters according to the formula 10 (M = $M_2$) are terephthalic acid, isophthalic acid, phthalic acid, methylterephthalic acid, naphthalenedicarboxylic acid, diphenyldicarboxylic acid, diphenylmethanedicarboxylic acid, adipic acid, succinic acid, glutaric acid, sebacic acid, pimelic acid, suberic acid, azelaic acid, diglycollic acid, cyclohexanedicarboxylic acid and cyclohexanediacetic acid. The preferred lower aliphatic esters of such acids are dimethyl esters, diethyl esters and dipropyl esters and mixtures of these.

Examples of glycols which can be used are: ethylene glycol, diethylene glycol and triethylene glycol, 1,2-propanediol and 1,3-propanediol, 1,4-, 2,3- and 1,3-butanediol, 1,6-hexanediol, 1,10-decanediol, cyclohexanedimethanol, cyclohexanediol, 2,2-dimethylpropanediol-(1,3), glycerine monomethyl ether and mixtures of the dihydric alcohols.

Suitable diphenols which can be used are those already mentioned in connection with the synthesis of the polycarbonates.

Several processes are available for the preparation of polyamides with 8-hydroxyquinoline end groups according to the formula 10 (M = $M_3$), based on preferably aliphatic diamines and aliphatic or aromatic dicarboxylic acids as well as the 8-hydroxyquinolines of the formula 1 (X = $NH_2$ or NH—($C_1$-$C_4$)-alkyl).

A customary process is the reaction of bifunctional acid chlorides, such as, for example, sebacyl chloride, with suitable diamines, such as, for example, hexamethylenediamine and the appropriate functional 8-hydroxyquinolines of the formula 1 (X = $NH_2$ or NH—($C_1$-$C_4$-alkyl), wherein the bis-acyl chloride, in a water-immiscible organic solvent, for example tetrachloroethylene, is reacted with the aqueous solution of the diamine and of the hydroxyquinoline of the formula 1 which is to be used, in a phase boundary condensation. This process makes it possible to use in particular those reactants where a thermal polycondensation presents difficulties. The reaction is run at temperatures around 20° C. and below, and in general the sum of the two amine components can be added in a slight excess relative to the bifunctional acid chloride.

(Literature: E. L. Wittbecker and P. Morgan, J. Polymer Sci. 40, 289 (1959) and P. W. Morgan and S. L. Kwolek, J. chem. Educ. 36, 182, 530 (1959)).

A further process permits the direct polycondensation of diamine, dicarboxylic acids and the functional 8-hydroxyquinolines of the formula 1 (X = $NH_2$ or NH—($C_1$-$C_4$-alkyl), in which case the water produced in the reaction must be removed continuously from the reaction space, for example by vacuum, since it is a reaction parameter having a substantial influence on the rate of polyamide formation. This process is carried out in bulk or in an inert diluent, for example xylenol, at temperatures of 180°-250° C.

Since the reaction in the first place produces a salt, it is also possible to employ directly the salt obtained beforehand from the corresponding diamines and dicarboxylic acids. (Literature: DRP 749,747 (1935), Du Pont; Laboratory Instructions by W. Lehmann, Bayer AG, see Houben-Weyl, Methoden der Org. Chemie (Methods of Organic Chemistry), volume XIV, 2, page 136 (1963), Thieme Verlag, Stuttgart).

Suitable dicarboxylic acids and their derivatives are the bifunctional acids already mentioned in connection with the preparation of the polyesters with 8-hydroxyquinoline end groups. The following diamines are examples of suitable amine components: ethylenediamine, trimethylenediamine, tetramethylenediamine, pentamethylenediamine, hexamethylenediamine, decamethylenediamine, 4,4'-diamino-dicyclohexylmethane and m- and p-phenylenediamine, and diphenyldiamine.

The diamines and dicarboxylic acids can of course also optionally be co-condensed with suitable aminocarboxylic acids such as, for example, 6-amino-caproic acid, 11-aminoundecanoic acid or their lactams, in the form of a melt condensation with exclusion of oxygen (literature: M. R. Aélion, Annales de Chemie (12) 3, 5 (1948)).

A further subject of the present specification is thus a process for the preparation of the compounds of the formula 10, which is characterised in that for the preparation of the polycondensates of the structural part M in accordance with known processes, 8-hydroxyquinolines of the formula 1 are used as reactants.

The polycondensates according to the invention, carrying 8-hydroxyquinoline end groups, in accordance with the formula 10, can be employed, in a suitable form, for removing metal ions of the transition elements of the periodic system, that is to say the elements Sc to Zn (atomic numbers 21 to 30), Y to Cd (atomic numbers 39–48), La to Hg (atomic numbers 57–80), Ac to U (atomic numbers 89–92) and also Mg, Ca, Al, Pb and Bi from solutions or industrial effluents. The absorption of the metal ions is reversible; thus they can easily again be separated from the polycarbonate by washing, for example with acids or complex-forming agents.

The polycondensates according to the invention can also be employed for complexing interfering metallic impurities in thermoplastics or thermosetting resins in amounts of 0.01% by weight to 10% by weight, based on the total mixture.

The polycondensates according to the invention, of the formula 10, can also be used for the preparation of polymers containing metal.

The subject of the present specification thus also embraces a process for the preparation of polymers containing metal, of the following formula 11

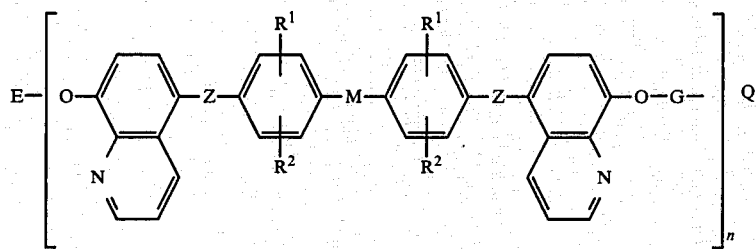

wherein Q is either a group of the formula 10 a or T and

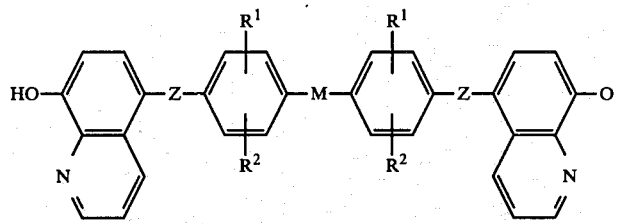

wherein
$R^1$, $R^2$, Z and M are defined in accordance with the formula 10,
n is between 1 and 50 and
G corresponds to the metal compounds of the formula

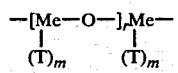

in which
m is the number of anion bonds and/or ligands T on the metal atom and is calculated from the difference of the valency or co-ordination number minus two,
r is an integer from 0 to 20,
Me is a metal of sub-group 1 to 8 or of main group 2 to 5, especially one of the elements Sc to Zn (atomic numbers 21 to 30), Y to Cd (atomic numbers 39 to 48), La to Hg (atomic numbers 57 to 80), Ac to u (atomic numbers 89 to 92), Al, Pb and Bi, and
T corresponds to anions of inorganic mineral acids, anions of organic carboxylic acids, complex-forming agents, $C_1$-$C_{18}$-alkoxy radicals, $C_6$-$C_{12}$-aryloxy radicals and/or trialkylsiloxy radicals with 3 to 12 C-atoms and E is H or

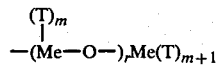

which is characterised in that the polycondensates of the formula 10 are reacted with metal compounds of the formula 12

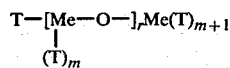

a. in homogeneous solution in aprotic solvents at temperatures between 20° C. and 160° C. using molar ratios of the compounds 10:12 which are between 1:0,5 and 1:1 and using concentrations of 10 and 12 in solution which are between 0.001% by weight and 30% by weight, or b. if T only corresponds to anions of inorganic mineral acids, anions of organic caboxylic acids and/or complex-forming agents, by two-phase reaction of the compounds of the formula 10 in aprotic solvents and of the compounds of the formula 12 in polar protic solvents at temperatures between 20° C. and 220° C., in a molar ratio of the compounds 10:12 of between 1:0,5 and 1:1 and in concentrations of 1–30% by weight of the polycondensates of the formula 10 and of 0.001–30% by weight of the metal compounds of the formula 12. Inorganic mineral acids useful for preparing anions T are especially HCl, $H_2SO_4$, $H_3PO_4$ and $HNO_3$; organic carboxylic acids useful for preparing anions T are especially saturated alliphatic $C_1$-$C_{18}$ carboxylic acids (e. g. HCOOH $(COOH)_2$, $CH_3$—COOH and $CH_3$—$(CH_2)_{16}$—COOH); as complex forming agents are suitable especially aliphatic diketones (e.g. acetylacetone) ethylendiamintetraacetic acid, nitrilotriacetic acid and cyclopentadien.

The subject of the present specification thus also embraces polymers 11 containing metal, prepared using the polycondensates of the formula 10 in accordance with the abovementioned processes.

In the polymers according to the invention, containing metal, of the formula 11, obtained by reaction of polycondensates of the formula 10 with metal compounds of the formula 12, the polycondensates, containing 8-hydroxyquinoline end groups, are linked via the metals or metal oxides in general by linear chain formation, with stable inner complexes of the 8-hydroxyquinoline radicals with the metals being formed. (Compare R. Berg "Die analytische Verwendung von o-Oxychinolin ("Oxin") und seiner Derivate" ("The Analytical Use of o-Hydroxyquinoline ("Oxine") and of its Derivatives"), 2nd edition, Stuttgart 1938, and R. Bock, Angew. Chemie 67, 420 (1955) ).

A partial branching or crosslinking of the linear polymers, containing metal, of the formula 11 can however be achieved subsequently by reaction of the ligands T still present on the metal compounds of the formula 12 a.

Thus, for example, when using titanium tetrabutylate as the metal compound for linking polycondensates of the formula 10, the butoxy radicals remaining on the titanium after the chain lengthening reaction can be split off on addition of water and the titanium atoms of different polymer chains bonded to one another by oxygen bridges.

The linear chain lengthening can be observed from the rise in the relative viscosity and from determination of the numerical average $M_n$ from osmometric measurements.

The desired chain length can be obtained by varying the molar ratio of metal compound to polycondensate of the formula 10.

With a molar ratio of polycondensate 10 to metal compound of 1:1 linear polymers 11 are obtained, with a molar ratio of polycondensate 10 to metal compound of 1:0,5 dimeric products of formula 11 are obtained.

Equally, the metal content of the polymers of the formula 11 can be varied in accordance with the amount of metal compound employed and can be up to 30% by weight, referred to the polymer 11 in question.

Examples of suitable metal compounds for the preparation of the polymers, containing metal, of the formula 11, are the following compounds of the metals of the 1st to 8th sub-group and of the 2nd to 5th main group:

a. Inorganic salts and their aquo-complexes, such as, for example, $FeCl_3$, $FeCl_3 \times 6 H_2O$, $CuSO_4$, $CuSO_4 \times 5 H_2O$, $CrCl_3 \times 6 H_2O$, $CoCl_2$, $MnSO_4 \times 7 H_2O$, $NiSO_4 \times 6 H_2O$, $AlCl_3 \times 6 H_2O$;

b. Salts of organic acids, such as, for example, $Cu(C_2H_3O_2)_2$, $Ni(C_2H_3O_2)_2$, $Co(C_2H_3O_2)_2$, $Zn(C_2H_3O_2)_2$, $Cu(C_7H_5O_2)_2$, $AgC_7H_5O_2$, $ZnC_2O_4$, $CrC_2O_4$, $CoC_2O_4$ 33 2 $H_2O$ c. Alcoholates and phenolates, such as, for example, $Zr(C_4H_9O)_4$, $Ti(C_4H_9O)_4$, $Zr(C_{18}H_{37}O)_4$, $Ti(C_{18}H_{37}C_4)_4$, $Ti(CH_3C_6H_4O)_4$, $B(C_2H_5O)_3$, $B(C_4H_9O)_3$ d. Metal complexes, such as, for example, the acetylacetonates $Co(C_5H_7O_2)_2$, $Ni(C_5H_7O_2)_2$, $Fe(C_5H_7O_2)_3$, $Mn(C_5H_7O_2)_2$, $Zr(C_5H_7O_2)_4$ and bis-(cyclopentadienyl)-titanium dichloride.

e. Aggregated metal compounds such as, for example, n-butyltitanate polymer, cresyl-titanate polymer and (trimethylsiloxy) -titanate polymer.

In these, the degree of polymerisation can be between 1 and 20. (See the corresponding company publication by Dynamit Nobel).

The reaction of the abovementioned metal compounds with the polycondensates of the formula 10 can be carried out in homogeneous solution or as a phase boundary reaction.

The reaction in homogeneous solution is carried out in aprotic solvents such as, for example, acetone, acetonitrile, nitromethane, benzene, toluene, xylene, monochlorobenzene and dichlorobenzene, dimethylformamide and dimethylacetamide, dichloroethane, methylene chloride, chloroform, diethers of ethylene glycol and the like. The starting compounds can be brought together direct, preferably in the form of solutions of defined composition, of which the concentration range is from 0.001 to 30% by weight of starting compound in solution, using ratios of equivalent solved reactants of 8-hydroxyquinoline/ polycondensate and metal compound of between 1:0,5 and 1:1, at temperatures between 20° C. and 160° C., it being more advantageous to add the metal compounds to the polycondensates, containing 8-hydroxyquinoline end groups, of the formula 10.

In the phase boundary reaction, the polycondensates of the formula 10 are dissolved in aprotic and water-immiscible solvents such as, for example, benzene, toluene, xylene, monochlorobenzene and dichlorobenzene and chlorinated hydrocarbons such as, for example, dichloroethane, methylene chloride, chloroform and the like. The metal compounds of the formula 12, in which T can only represent anions of inorganic mineral acids, anions of organic carboxylic acids and/or complex-forming agents, are employed as a solution in a protic solvent, preferably water. In the phase boundary reaction, it is possible to use a greater excess of metal compound of the formula 12, since unreacted metal compound remains in the protic solvent. The reactions are carried out at temperatures between 20 and 220° C. and in concentrations of 1–30% by weight as regards the polycondensates of the formula 10 and between 0.001 and 30% by weight as regards the metal compounds of the formula 12.

The metal-containing polymers of formula 11 have because of their metal content an increased resistance to heat (measured according DIN 53 735), an increased resistance to chemicals (measured according DIN 53 476), a higher glass transition temperature and a reduced stress cracking (measured according DIN 53 449) compared to the corresponding metal-free polycondensates with 8-hydroxyquinoline end groups of formula 10.

Both types of polycondensate compounds, the metal-free of formula 10 and the metal-containing of formula 11 are according the polymer segments M of technical and commercial use: Thus the polycarbonates of formulae 10 and 11 based on $M_1$ according the corresponding polycarbonates with the end groups known in the art (e.g. p-tert.-butylphenyl-end groups) instead of those derived from the 8-hydroxychinolines of formula 1 according the instant invention; the polyesters of formulae 10 and 11 based on $M_2$ according the corresponding polyesters with the end groups known in the art instead of those derived from the 8-hydroxychinolines of formula 1 according the instant invention; the polyamides of formulae 10 and 11 based on $M_3$ according the corresponding polyamides with the end groups known in the art instead of those derived from the 8-hydroxychinolines of formula 1 according the instant invention.

From the use of the 8-hydroxychinolines of formula 1 as end groups for the polycondensates of the types $M_1$, $M_2$ and $M_3$ of formula 10 there result the additional, already mentioned (page 11) complexing properties of these polycondensates; from the reaction of the compounds of formula 10 to the metal-containing of formula 11 according to instant specification there result the improved properties mentioned above.

Hence, the subject of the present patent application also includes new polymers, containing metal, of the formula 11

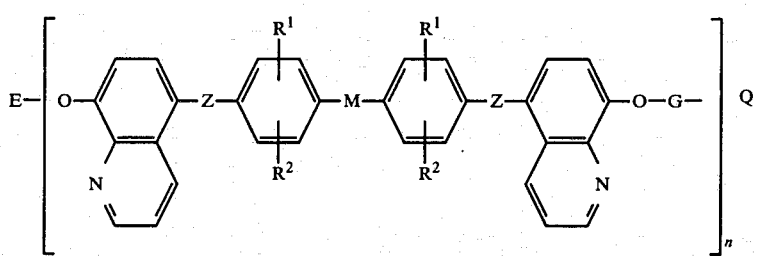

wherein
Q is either a group of the formula 10 a or T, and wherein $R^1$, $R^2$, Z and M are defined in accordance with formula 10,
n is between 1 and 50 and
G corresponds to the metal compounds of the formula 12 a

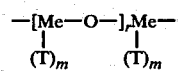      12 a in which
m is the number of anion bonds and/or ligands T on the metal atom and is calculated from the difference of the valency or co-ordination number minus two,
r is an integer from 0 to 20,
Me is a metal of sub-group 1 to 8 or of main group 2 to 5, especially one of the elements Sc to Zn (atomic numbers 21 to 30), Y to Cd (atomic numbers 39 to 48), La to Hg (atomic numbers 57 to 80), Ac to U (atomic numbers 89 to 92), Al, Pb and Bi, and T corresponds to anions of inorganic mineral acids, anions of organic carboxylic acids, complex-forming agents, $C_1$-$C_{18}$-alkoxy radicals, $C_6$-$C_{12}$-aryloxy radicals and/or trialkylsiloxy radicals with 3 to 12 C-atoms and
E is H or

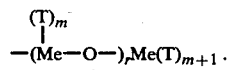

The polymers according to the invention, containing metal, of the formula 11, can be used, by themselves or as a constituent of a polymer blend, for the production of weathering-resistant, corrosion-resistant, solvent-resistant and heat-resistant coatings, as sizing agents and as adhesion promoters between metals, metal oxides, glass surfaces and subsequently applied plastics and lacquers. The metal-containing polymers 11 are suitable products for all those purposes, where usually the corresponding polycarbonates, polyesters or polyamides are used.

The polymers according to the invention, containing metal, of the formula 11, can be used as stabilisers for plastics. Such plastics are polyvinyl chloride or its copolymers such as ethylene/vinyl chloride copolymer or vinyl acetate/vinyl chloride copolymer, polyethylene, polypropylene, polyacrylates, copolymers of acrylates or methacrylates and at least one further monomer, vinyl acetate polymers, ethylene/vinyl acetate copolymers, polycarbonates, polysulphones, polyphenylene oxides, styrene copolymers, polymers of the ABS type (acrylonitrile-butadiene-styrene graft polymer thermoplastics), polyamides of the nylon type or polycaprolactam, polyethylene terephthalates, polyacetals and the like.

In addition, the polymers containing metal, of the formula 11, can be used as catalysts and, for example in the form of the cobalt compounds, as initiators for reactions which take place by a radical mechanism.

The following description of the starting compounds for the polycondensates 10, namely the new functional 8-hydroxyquinolines of the formula 1

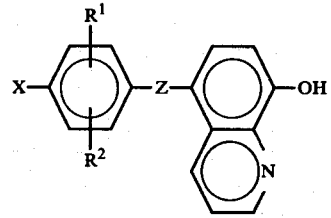

in which
X represents OH or $NH_2$ or NH—($C_1$-$C_4$)-alkyl, $R^1$ and $R^2$ are identical or different and denote hydrogen, ($C_1$-$C_4$)-alkyl, phenyl or halogen (for example, chlorine or bromine) and
Z is $CH_2$, CH—$CH_3$, an isoalkylidene radical with 3 to 5 carbon atoms, a cycloalkylene or cycloalkylidene radical with 5 to 15 carbon atoms, or a radical of the formulae 2

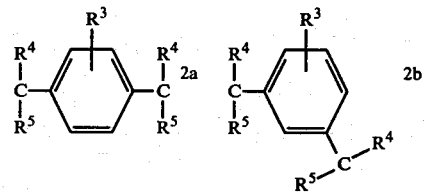

in which
$R^4$, $R^5$ and $R^3$ are identical or different alkyl radicals with 1 to 5 carbon atoms,
is taken mainly from the German Patent Application P 24 07 308 (Le A 15 355).

As isoalkylidene radicals Z of formula 1 there are to be understood the radicals

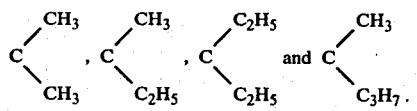

Suitable process for the preparation of the functional 8-hydroxyquinolines of formula 1 are the reaction of 8-hydroxyquinoline with (cyclo)alkenyl-substituted phenols or (cyclo)alkenyl-substituted anilines or with compounds which are also able to form carbonium ions under the influence of acid catalysts, say halogenoalkyl-substituted phenols or anilines or hydroxyalkyl-substituted phenols or anilines, according to the methods, which are in themselves known, for the alkylation of hydroxyaryl compounds, in which methods it is also possible for the components suitable for the alkylation of 8-hydroxyquinoline, for example the hydroxyalkyl-substituted phenols, only to be produced in situ, for example from corresponding phenols and corresponding aldehydes, during the alkylation of 8-hydroxyquinoline.

The compounds of the formula 1 in which $Z = CH_2$ are obtained by reaction of 8-hydroxyquinoline with compounds of the formula 3

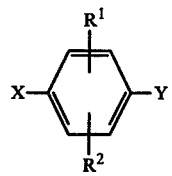

3 in which
X, $R^1$ and $R^2$ have the same meaning as in the formula 1 and in which
Y represents the hydroxymethyl or halogenomethyl radical the molar ratio of the reactants (8-hydroxyquinoline to compounds of the formula 3) preferably being between 1:1 and 10:1.

In the case of compounds of the formula 3 in which Y is halogenomethyl, preferably chloromethyl and bromomethyl, it is only possible to use Lewis acids such as, for example, aluminium-(III) chloride or boron trifluoride, as the catalysts, in amounts between 10 mol % and 100 mol %, relative to compounds of the formula 3.

Preferably, compounds of the formula 3, with Y being hydroxymethyl, are employed; these are easily obtainable from formaldehyde and the corresponding phenols and anilines. Alkylation catalysts used for this purpose are Lewis acids, hydrosilicates of the montmorillonite type and mineral acids and carboxylic acids which can, as for example in the case of acetic acid, also be used directly as solvents, in amounts between 10 mol % and 500 mol %, relative to compounds of the formula 3.

Depending on the nature of the starting substances and of the catalyst, the reaction can be carried out in bulk or in solution and in a temperature range of 10°–150° C., the choice of the solvent depending on the solubility of the starting materials, the reaction temperature and, especially the catalyst.

Only those solvents can be selected which are not alkylated under the particular reaction conditions and which themselves do not have an alkylating action, such as, for example, carbon disulphide, nitromethane, nitrobenzene, and, if appropriate, carboxylic acids, such as, for example, formic acid or acetic acid, and, in the absence of Lewis acids as catalysts, chlorinated aliphatic hydrocarbons, for example methylene chloride or dichloroethane, if appropriate. (Literature: Houben-Weyl, Methoden der organischen Chemie (Methods of Organic Chemistry), volume V/1a, page 509, Thieme Verlag, Stuttgart 1970).

The compounds of the formula 1, in which
Z is CH–CH$_3$, an isoalkylidene radical with 3 to 5 carbon atoms, a cycloalkylidene radical, with 5–15 C atoms or a radical of the formulae 2
are obtained by reaction of 8-hydroxyquinoline with compounds of the formula 3

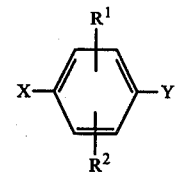

in which
X, $R^1$ and $R^2$ have the same meaning as in the formula 1 and in which
Y is vinyl, an alken-(1)-yl-(2) radical with 3 to 5 C atoms, an alken-(2)-yl-(2) radical with 4 to 5 C atoms, an alken-(2)-yl-(3) radical with 5 C atoms, a cycloalken-(1)-yl-(1) radical with 5 to 15 C atoms or a radical of the formulae 4

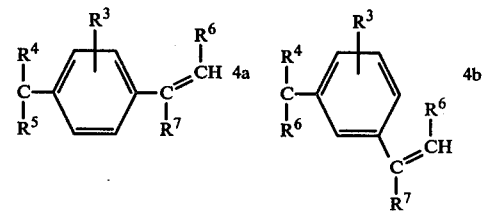

wherein
$R^3$, $R^4$, $R^5$ and $R^7$ are identical or different and denote alkyl radicals with 1–5 C atoms and $R^6$ is H or a $C_1$–$C_4$-alkyl radical.

The alkenyl or cycloalkenyl radicals in the compounds of the formula 3 can also be present masked as HCl adducts or $H_2O$ adducts. When using the $H_2O$ adducts, it is preferred to employ proton acids, such as, for example, hydrofluoric acid or sulphuric acid, as the catalyst, in which case the alkylation is preceded by the dehydration of the alcohol to the olefine. Lewis acids can also be used as catalysts (literature: A. Schriesheim in G. A. Olah, Friedel Crafts and Related Reactions, vol. II, page 477, Interscience Publishers, New York, London, Sidney 1964). The alkylation by means of the corresponding halides is also catalysed by Lewis acids. To avoid excessive isomer formation, the alkylation via the alcohols and halides is carried out at temperatures as low as possible in the range from 10° to 150° C., in bulk or in solution, using the solvents which have already been mentioned above.

The preferentially used alkylation of 8-hydroxyquinoline with the (cyclo)alkenyl compounds of the formula 3 is carried out in bulk or in solution, at temperatures between 50° and 250° C., preferably between 100° and 200° C., using acid catalysis with Lewis acids, hydrosilicates and proton acids. The catalyst is added in amounts of 10 to 200 mol %, depending on the starting substances, and the molar ratio of the reactants, olefinic alkylating agent to 8-hydroxyquinoline, is generally preferentially between 1:1 and 1:10, but can also lie outside this range. Suitable catalysts to be used are Lewis acids such as, for example, aluminium-(III) chloride, iron-(III) chloride, tin chloride, titanium tetrachloride, boron trifluoride and mixed catalysts of the type of AlCl$_2$.HSO$_4$ or AlBr$_2$.H$_2$PO$_4$, or proton acids such as, for example, hydrogen chloride, hydrofluoric acid, concentrated phosphoric acid, sulphuric acid from a concentration of 96% upwards, oxalic acid and toluenesulphonic acid. Acid activated aluminas such as bentonites, zeolites and other hydrosilicates, and ion exchange resins such as, for example, those based on polystyrenes carrying sulphonic acid groups, or phenolic resins, carrying sulphonic acid groups, which are insoluble in the reaction mixture, are also advantageous. The alkylation of 8-hydroxyquinoline with the (cyclo)alkenyl compounds can be carried out in bulk and in solution.

Examples of suitable solvents are nitrobenzene, nitromethane and carbon disulphide.

(Literature on the catalysis: V. N. Ipatieff and L. Schmerling, in Advances in Catalysis, volume 1, pages 27–64, Academic Press Inc. Publishers, New York 1950; literature on the alkylation with olefines: G. A. Olah, Friedel Crafts and Related Reactions, Vol. I, Interscience Publishers, New York, London, Sidney, 1963; F. Asinger et al. Erdöl, Kohle 20, 786, 852 (1967)).

The compounds of the formula 1, in which Z is a cycloalkylene radical with 5 to 15 C atoms, are obtainable by reaction of 8-hydroxyquinoline with compounds of the formula 3, in which Y is a corresponding hydroxy-cycloalkyl radical with 5–15 C atoms, though isomerisations at the cycloalkyl radical cannot be avoided entirely.

The subject of P 24 07 308 (Le A 15 355) thus also embraces a process for the preparation of the compounds of the formula 1; this is characterised in that 8-hydroxyquinoline is alkylated with compounds of the formula 3 in which X, R$^1$ and R$^2$ have the same meaning as in the formula 1 and Y is hydroxymethyl or halogenomethyl, vinyl, an alken-(1)-yl-(2) radical with 3–5 C atoms, an alken-(2)-yl-(2) radical with 4 to 5 C atoms, an alken-(2)-yl-(3) radical with 5 C atoms, a cycloalken-(1)-yl-(1) radical with 5 to 15 C atoms or a radical of the formulae 4, or a hydroxycycloalkyl radical with 5–15

C atoms
in the presence of acid catalysts, in accordance with the known methods for the alkylation of hydroxyaryl compounds, with the molar ratio of the reactants 8-hydroxyquinoline and a compound of formula 3 being between 1:1 and 10:1.

Instead of the (cyclo)alkenyl-substituted phenols or anilines of the formula 3 it is also possible to employ corresponding compounds which are also capable of forming, under the influence of acid catalysts, carbonium ions of the formula 1a

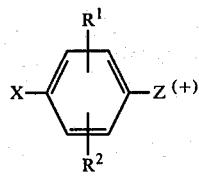

wherein X, R$^1$, R$^2$ and Z have the meaning of formula 1.

Examples of compounds which are suitable for the alkylation of 8-hydroxyquinoline, in accordance with the invention, are the following types of phenol obtainable according to DT-AS (German Published Specification) No. 1,235,894 and aniline types obtainable according to DT-AS (German Published Specification) No. 1,191,363 or according to DT-OS (German Published Specification) No. 2,064,305: 4-isopropylphenol, 2-methyl-4-isopropenylphenol, 2,6-dimethyl-4-isopropenylphenol, 2-propyl-4-isopropenylphenol, 2-phenyl-4-isopropenylphenol, 2-chloro-4-isopropenylphenol, 3-methyl-4-isopropenylphenol, 2-(p-hydroxyphenyl)-2-butene, 2-(p-hydroxyphenyl)-2-pentene, 4-cyclohexenylphenol, 2-(p-hydroxyphenyl)-2-(p-isopropenylphenyl)-propane, p-isopropenylaniline and p-isopropenylanilines which are substituted in the phenyl nucleus by aryl, for example phenyl, alkyl, for example C$_1$-C$_4$-alkyl, or halogen, for example chlorine or bromine.

Instead of the monomeric alkenylphenols and alkenyl-anilines it is equally well possible to use the dimers of these compounds, since these re-dissociate to the monomers under the chosen reaction conditions. Dimeric isopropenylphenol of the following formula

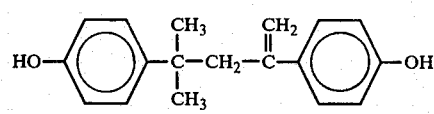

may be mentioned as an example.

Other compounds which are suitable, in the present context, for alkylating 8-hydroxyquinoline and are able to form carbonium ions under the influence of acid catalysts are, for example: 4-hydroxy-benzyl alcohol, 2-bromo-4-hydroxybenzyl alcohol, 3,5-dibromo-4-hydroxy-benzyl alcohol, 4-hydroxy-3,5-dimethyl-benzyl alcohol, 4-hydroxy-2,6-dimethylbenzyl alcohol, 4-hydroxy-2-isopropyl-5-methyl-benzyl alcohol, 2-phenyl-benzyl alcohol, 3-phenyl-benzyl alcohol, 2-[4-hydroxyphenyl]-propanol, 1-[4-hydroxyphenyl]-ethanol, 2-[4-hydroxyphenyl]-ethanol, 2-[4-hydroxyphenyl]-2-[4-(1-hydroxypropyl-(2))phenyl]-propane, 4-amino-benzyl alcohol and 2-chloro-4-aminobenzyl alcohol.

The reaction mixture is worked up as follows: the catalyst is first removed, if necessary after neutralisation, and solvent which may be present, and 8-hydroxyquinoline, are then removed in accordance with known methods, for example by extraction, fractional crystallisation, vacuum distillation and steam distillation. Crystallisation of the residue which ramins, from suitable solvents such as, for example, benzene, toluene, ethanol, diethyl ether, acetone or mixtures of these solvents, gives the desired functional 8-hydroxyquinoles in good yields. They can be used direct for further reactions.

The following Examples A, B and C show the preparation of the compounds of formula 1:

EXAMPLE A

2-[4-Hydroxyphenyl]-2-[5-(8-hydroxyquinolyl)]-propane 1508 g of 8-hydroxyquinoline, 483 g of p-isopropenylphenol and 150 g of bentonite (acid catalyst K 20 from Messrs. Südchemie, Munich) are brought together and heated for 24 hours to 180° C. under reflux and under a nitrogen atmosphere. The reaction mixture is then filtered through a pressure filter in order to remove the solid catalyst.

After addition of methylene chloride/water, a part of the 2-[4-hydroxyphenyl]-2-[5-(8-hydroxyquinolyl)]-propane is obtained as crystals. The mixture which remains is subjected to a steam distillation, during which the 8-hydroxyquinoline employed in excess can be recovered. On renewed addition of methylene chloride, a further proportion of the functional hydroxyquinoline is obtained as crystals.

The two crystalline fractions when combined give a total yield of 460 g (46% of theory). After extraction in a Soxhlet extractor with benzene, colourless crystals, of melting point 139° C., are obtained from benzene.

| Analysis: | C | H | N |
|---|---|---|---|
| Calculated | 77.4% | 6.10% | 5.01% |
| Found | 77.5% | 6.03% | 4.87% |

EXAMPLE B

2-[4-Aminophenyl]-2-[5-(8-hydroxyquinolyl)]-propane 2180 g of 8-hydroxyquinoline, 400 g of β-isopropenylaniline and 300 g of bentonite (acid catalyst K 20 of Messrs. Südchemie, Munich) are heated to 160° C. for 26 hours under reflux and under a nitrogen atmosphere. The reaction mixture is filtered through a pressure filter and is then successively subjected first to a vacuum distillation and then to a steam distillation. In the course thereof, the 8-hydroxyquinoline employed in excess is recovered almost quantitatively. Methylene chloride is then added to the reaction mixture and the organic phase is separated off. The residue which remains after concentrating the organic phase is extracted with a methylene chloride/petroleum ether mixture and 382 g (46% of theory) of 2-[4-aminophenyl]-2-[5-(8-hydroxyquinolyl)]-propane of melting point 105°–107° C. are obtained. The melting point of the colourless crystals rises to 109° C. on recrystallisation from ethanol.

| Analysis: | C | H | N |
|---|---|---|---|
| Calculated | 77.7% | 6.46% | 10.02% |
| Found | 77.5% | 6.58% | 9.88% |

EXAMPLE C

[4-Hydroxy-3,5-dimethyl-phenyl]-[5-(8-hydroxyquinolyl)]-methane 36.2 g of 8-hydroxyquinoline are solved in 200 ml acetic acid and at the boiling point of this solution within one hour a solution of 7.6 g of 2,6-dimethyl-4-hydroxy-methylene-phenol in 50 ml acetic acid is added dropwise. The mixture is boiled for 5 hours under reflux, threafter acetic acid is withdrawn by vacuum-distillation and aceotropic distillation. The non-reacted 8-hydroxyquinoline is removed by water distillation. The remaining compound is solved in $CH_2Cl_2$ and filtered. By evaporation of the $CH_2Cl_2$ 7.1 g of colourless crystals are obtained. Yield 47% of the theoretical amount.

| Analysis: | C | H | N |
|---|---|---|---|
| Calculated | 77.5% | 6.10% | 5.01% |
| Found | 77.2% | 6.22% | 5.04% |

The examples which follow describe the preparation of some polycondensates, containing 8-hydroxyquinoline end groups, of the formula 10, and of some polymers containing metal, of the formula 11 and the use of the polycondensates of formula 10.

EXAMPLE 1

456 g of bisphenol A and 559 g of 2-[4-hydroxyphenyl]-2-[5-(8-hydroxyquinolyl)]-propane are dissolved in 4 kg of 9% strength sodium hydroxide solution and 9 kg of methylene chloride are then added. 562.8 g of phosgene are introduced with vigorous stirring and 60 ml of a 4% strength triethylamine solution are then added dropwise. The mixture is stirred for a further hour and if necessary sufficient sodium hydroxide solution is added for the pH of the solution to remain constant at 13. The phases are separated and the aqueous phase is tested for complete conversion. The organic phase is extracted once with 5% strength $H_3PO_4$, washed with water until neutral and subsequently dried over sodium-sulphate. The organic phase is concentrated and the short-chain polycarbonate with hydroxyquinoline end groups is obtained direct by precipitation in methanol. $\eta_{rel}$: 1.038 ($\eta_{rel}$ is measured in $CH_2Cl_2$ at 20° C.; 0.5 g solved in 100 g solution); nitrogen analysis: $N_2$ 2.56%; phenolic OH: 2.8%. The molecular weight calculated from these values is $M_n = 1178$.

EXAMPLE 2

456 g of bisphenol A and 7 g of 2-[4-hydroxyphenyl]-2-[5-(8-hydroxyquinolyl)]-propane are dissolved in 2.675 kg of 9% strength sodium hydroxide solution. 6 kg of methylene chloride are then added and 280 g of phosgene are introduced with vigorous stirring. Thereafter, 30 ml of a 4% strength triethylamine solution are also added and the mixture is stirred for a further hour, during which the pH of the solution is kept at 13 by addition of sodium hydroxide solution. Working up takes place as in Example 1. $\eta_{rel}$: 1.517 ($\eta_{rel}$ measured according to Example 1). $M_n = 17800$ (determined by membrane osmometry in dioxane).

EXAMPLE 3

114 g of bisphenol A, 9.30 g of 2-[4-hydroxyphenyl]-2-[5-(8-hydroxyquinolyl)]-propane and 40 g of sodium hydroxide are dissolved in 3 l of water. Thereafter, 300 ml of a 10% strength sodium lauryl-sulphate solution are also added. The reaction solution is stirred vigorously and 101.6 g of isophthalic acid dichloride in 3 l of methylene chloride are then also added. The resulting emulsion is stirred for a further 5 minutes and the product is then precipitated in acetone. The polymer, containing hydroxyquinoline end groups, which is formed is filtered off and washed with water and acetone. The polyester purified in this way is dried in vacuo.

$\eta_{rel}$: 1.035 ($\eta_{rel}$ measured according to Example 1). $M_n = 5500$ (determined osmometrically in dioxane).

EXAMPLE 4

7.65 g (7 mmols) of the polycarbonate with hydroxyquinoline end groups ($M_n = 1096$) described in Example 1 are dissolved in 150 ml of absolute $CH_2Cl_2$ and a solution of 3.4 g of titanium tetra-butylate in 100 ml of absolute $CH_2Cl_2$ is added progressively in 10 ml portions, the relative viscosity being determined, as a measure of the growth of the molecular weight, after the addition of each 10 ml of the titanium tetra-butylate solution. Table I below shows the relationship between the rising viscosity and the particular amount of metal compound added.

Table 1

| Material taken | Addition | Ratio of equivalents of polycondensate/ metal compound | τrel |
| --- | --- | --- | --- |
| 7.65 g of polycarbonate with hydroxyquinoline end groups ($M_n = 1096$) | 10 ml of solution I$^x$ | 7:1 | 1.055 |
| " | 20 ml of solution I$^x$ | 7:2 | 1.066 |
| " | 30 ml of solution I$^x$ | 7:3 | 1.082 |
| " | 40 ml of solution I$^x$ | 7:4 | 1.093 |
| " | 50 ml of solution I$^x$ | 7.5 | 1.142 |

$^x$Solution I: 3.4 g of titanium tetra-butylate in 100 ml of $CH_2Cl_2$ Standard according to Example 1 1.038

EXAMPLE 5

1.78 g of the polycarbonate, containing hydroxyquinoline end groups ($M_n = 17800$), prepared in Example 2 are dissolved in 100 ml of absolute $CH_2Cl_2$ and 10 ml of this solution are taken. To this is added a solution of 3.83 g of zironium tetra-butylate in 1 l of absolute $CH_2Cl_2$ in 1 ml portions introduced dropwise, and after each addition the relative viscosity is determined, as in Example 4.

Table 2

| Material taken | | Ratio of equivalents of polycondensate/ metal compound | τrel |
| --- | --- | --- | --- |
| 1.78 g of polycarbonate with hydroxyquinoline end groups (Mn = 17800) | 1 ml of solution II$^{x)}$ | 10:1 | 1.714 |
| " | 2 ml of solution II$^{x)}$ | 10:2 | 1.844 |
| " | 3 ml of solution II$^{x)}$ | 10:3 | 2.083 |
| " | 4 ml of solution II$^{x)}$ | 10:4 | 2.419 |
| " | 5 ml of solution II$^{x)}$ | 10:5 | 2.635 |
| " | 6 ml of solution II$^{x)}$ | 10:6 | 2.705 |

$^{x)}$Solution II: 3.83 g of zirconium tetra-butylate in 1 l of $CH_2Cl_2$ Standard according to Example 2 1.517

EXAMPLE 6

5 g of the polycarbonate ($M_n = 17800$) prepared in Example 2 are dissolved in 180 ml of absolute $CH_2Cl_2$ and 14 ml, 21 ml and 28 ml of a solution of 0.383 g of zirconium tetrabutylate in 100 ml of absolute $CH_2Cl_2$ are added dropwise. The resulting chain-lengthened polycarbonates containing zirconium were isolated and converted to films. Table 3 shows the yield stress $\delta_S$, the tensile strength $\delta_R$, the elongation at break $\epsilon_R$ and the modulus of elasticity of the films and relates these to the metal content of the particular polycondensate.

Table 3

| Ratio of equivalents of polycondensate/ metal compound | δ S (kp/cm$^2$) | δ R (kp/cm$^2$) | ε R % | E-modulus (kp/cm$^2$) |
| --- | --- | --- | --- | --- |
| 1 : 0,5 | 533 | 509 | 69.3 | 27000 |
| 1 : 0,75 | 500 | 500 | 50.6 | 28400 |
| 1 : 1 | 516 | 500 | 50.8 | 29700 |

The yield stress, the tensile strength and the elongation at break are measured according DIN 53 455; the ε-modulus is measured according DIN 53 457.

EXAMPLE 7

24 g of a polycarbonate prepared according to Example 2, with 8-hydroxyquinoline end groups and a molecular weight $M_n = 11980$ (measured by membrane osmometry in dioxane) are dissolved in 200 ml of absolute $CH_2Cl_2$ and 0.476 g of titanium tetrabutylate in absolute $CH_2Cl_2$ is added.

The polycondensate containing metal was converted to a film and the modulus of elasticity (according DIN 53 457) and glass transition temperature thereof were determined. In addition, the molecular weight was determined osmometrically.

Table 4

| Ratio of equivalents of polycondensate/ metal compound | $M_n$ determined osmometrically $M_n$ of starting substance = 11980 | Glas transition temperature (° C) | E-modulus (kp/cm$^2$) |
| --- | --- | --- | --- |
| 2 : 1.4 | $M_n$18800 | 154.5 | 22700 |

EXAMPLE 8

8 g of a polycarbonate of $M_n = 16000$ (measured by membrane osmometry in dioxane), prepared according to Example 2, were dissolved in 100 ml of absolute $CH_2Cl_2$ and a solution of 0.32 g of titanium tetra-butylate polymer in 20 ml of $CH_2Cl_2$ was added. The resulting polycarbonate containing titanium was examined by differential thermo-analysis. Table 5 shows the glass transition temperature which has been raised by incorporation of the metal.

Table 5

| Ratio of equivalents of polycondensate/ metal compound | Glass transition temperature Polycondensate with hydroxy-quinoline end groups | Glass transition temperature Metal polycondensate | Heat stability according DIN 53735 |
| --- | --- | --- | --- |
| 1 : 0.5 | 145° C | 162° C | decomposition above 350° C |

EXAMPLE 9

1.78 g portions of the polycarbonate with 8-hydroxyquinoline end groups, prepared in Example 2, are reacted with the metal acetylacetonates listed in Table 6, in the molar ratio of 1:1, by heating to 140° C. in dichlorobenzene for two hours.

Table 6

| Material taken | Addition | Metal content (% by weight) | |
|---|---|---|---|
| | | calculated | found |
| 1.78 g of hydroxyquinoline-polycarbonate ($M_n$ = 17800) | 26 mg of cobalt acetylacetonate | 0.33 | 0.33 |
| " | 27 mg of nickel acetylacetonate | 0.33 | 0.34 |
| " | 35 mg of iron acetylacetonate | 0.32 | 0.31 |

It proved possible to convert all the polycarbonates containing metal to films. The film containing cobalt was tested tensometrically: according to DIN 53 455

| Tensile strength | $\delta R$ (kp/cm$^2$) : | 585 |
| Elongation at break | $\epsilon R$ % : | 51 |
| E-modulus (DIN 53 457) | (kp/cm$^2$) : | 28500 |

EXAMPLE 10

3 g portions of the polyester with 8-hydroxyquinoline end groups ($M_n$ = 5500), described in Example 3, are dissolved in 100 ml of absolute CH$_2$Cl$_2$ and the following metal alcoholate solutions are added in equivalent amounts:

1. 10 ml of a solution of 1.77 g of titanium tetra-butylate in 100 ml of absolute CH$_2$Cl$_2$,
2. 10 ml of a solution of 2 g of zirconium tetra-butylate in 100 ml of absolute CH$_2$Cl$_2$.

Table 7

| Material taken | Addition | Metal content (% by weight) | |
|---|---|---|---|
| | | calculated | found |
| 3 g of polyester with 8-hydroxyquinoline end groups ($M_n$ 5500) | 0.177 g of Ti(C$_4$H$_9$O)$_4$ | 0.83% | 0.75% |
| " | 0.200 g of Zr(C$_4$H$_9$O)$_4$ | 1.6% | 1.4% |

EXAMPLE 11

Polyester from aliphatic dicarboxylic acids

A mixture of 7,87 g of adipic acid dichlorid, 4,28 g of hydroquinone and 1.32 g of 2-[4-hydroxyphenyl]-2[5-(8-hydroxyquinolyl)]-propane and 20 ml of nitrobenzene are slowly in a heated dry atmosphere within 2.5 hours up to 150° C. and is kept at this temperature for a further 6 hours. During the total reaction an N$_2$-stream is passed through the reaction mixture. The nitrobenzene is distilled off under reduced pressure and the solid residue is dried. The polycondensate obtained has a molecular weight Mn of 7600 determined by membrane osmometry in dioxane.

EXAMPLE 12 Polyamide

A mixture of 55 g of N,N'-diethyl-ethylenediamine and 6.95 g of 2-(4-aminophenyl)-2-[5-(8-hydroxyquinolyl)]-propane and 106 g of Na$_2$CO$_3$ in 2.5 l of H$_2$O is throughly mixed. A solution of 101 g of terephthalic acid dichloride in 800 ml of dry CHCl$_3$ is added within 10 minutes. The CHCl$_3$ is distilled off from the reaction mixture; the polycondensate obtained is filtered off, washed with water four times: 98 g of a dried polycondensate is obtained having a $\eta_{rel}$ of 1.95 ($\eta_{rel}$ is determined in cresol at 25° C., 1% by weight solution).

EXAMPLE 13

Use of the polycarbonate of Example 1 as absorbing agent. 5 g of the polycarbonate of Example 1 are dissolved in 100 ml of CH$_2$Cl$_2$ and agitated with a solution of 2 g of

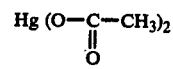

in 100 ml of H$_2$O for 2 hours at 20° C. Thereafter the phases are separated and the organic phase is dried. The resulting polymer contains 0.99 of Hg which corresponds to a content of 19.8% by weight. This shows the good capacity of the polycondensates of formula 10 for absorbing having metal ions.

EXAMPLE 14

Use of the polyamide of Example 12 as absorbing agent. According to Example 13 5 g of the polyamide of Example 12 are dissolved in chloroform and agitated together with a solution of 8.15 g of

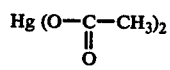

in 100 ml of H$_2$O for two hours at 20° C. The H$_2$O-phase is separated and the CHCl$_3$ is distilled off. The remaining polymer has an Hg-content of 5.1% by weight.

This shows the good capacity of the polycondensates of formula 10 for absorbing heavy metal ions.

The Hg-containing polymer has the structure of the products of formula 11 and is therefore an example for producing a metal-containing polyamide of formula 11.

What we claim is:

1. A polyamide of the formula

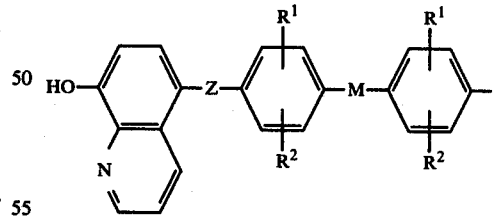

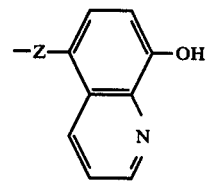

wherein
$R^1$ and $R^2$ are identical or different and denote hydrogen, (C$_1$-C$_4$)-alkyl, phenyl or halogen and Z is CH$_2$, CH—CH$_3$, an isoalkylidene radical with 3 to 5 carbon atoms, a cycloalkylene or cycloalkylidene radical with 5 to 15 carbon atoms, or a radical of the formula

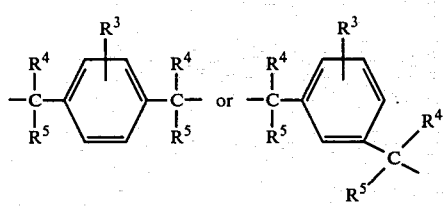

in which
R⁴, R⁵ and R³ are identical or different alkyl radicals with 1 to 5 carbon atoms, and M is a polyamide segment of the formula

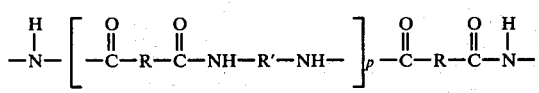

wherein
R and R' are identical or different and are $C_2$-$C_{12}$-alkylene which can be interrupted by -O- or cyclohexylene, $C_5$-$C_{15}$ cycloalklyene, $C_8$-$C_{12}$ arylenedialkylene, $C_6$-$C_{12}$ arylene and $C_{13}$-$C_{15}$ alkylidene diphenylene and p is an integer between 2 and 50.

2. A process for preparing polyamides according to claim 1 comprising co-condensing 2 to 28.5 mol % based on starting components of 8-hydroxyquinolines of the general formula

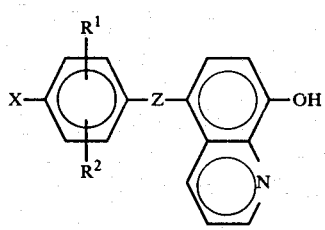

wherein
X is $NH_2$, $R^1$ and $R^2$ are identical or different and are hydrogen, ($C_1$-$C_4$)-alkyl, phenyl or halogen and Z denotes $CH_2$, CH—$CH_3$, an isoalkylidene radical with 3 to 5 carbon atoms, a cycloalkylene or cycloalkylidene radical with 5 to 15 carbon atoms or a radical of formula

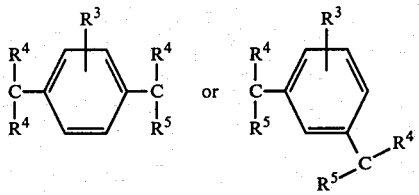

wherein
$R^3$, $R^4$ and $R^5$ are defined in claim 1 with bifunctional acid chlorides and diamines.

3. The process according to claim 2 wherein the bifunctional acid chlorides are the chlorides of the dicarboxylic acids selected from the group consisting of terephthalic acid, isophthalic acid, phthalic acid, methylterephthalic acid, naphthalenedicarboxylic acid, diphenyldicarboxylic acid, diphenylmethanedicarboxylic acid, adipic acid, succinic acid, glutaric acid, sebacic acid, pimelic acid, suberic acid, azelaic acid, diglycollic acid, cyclohexanedicarboxylic acid and cyclohexanediacetic acid and the diamines are selected from the group consisting of ethylenediamine, trimethylenediamine, tetramethylenediamine, pentamethylenediamine, hexamethylenediamine, decamethylenediamine, 4,4'-diamino-dicyclohexylmethane and m- and p-phenylenediamine, and diphenyldiamine.

4. A polyamide of the formula

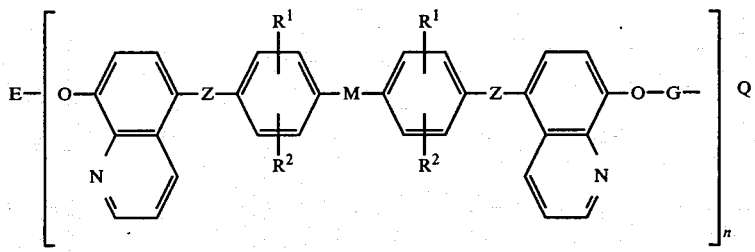

wherein
Q is either a group of the formula

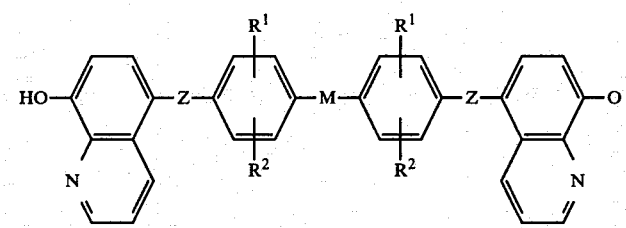

or T and wherein
$R^1$, $R^2$, Z and M are as defined in claim 1
n is between 1 and 50 and
G corresponds to metal compounds of the formula

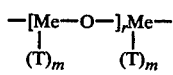

in which m is the number of anion bonds and/or ligands T on the metal atom and is calculated from the difference of the valency or co-ordination number minus two, r is an integer from 0 to 20, Me is a metal of sub-group 1 to 8 or of main group 2 to 5 of the periodic table and T corresponds to anions of inorganic mineral acids, anions of organic carboxylic acids, complex-forming agents, $C_1$–$C_{18}$-alkoxy radicals, $C_6$–$C_{12}$-aryloxy radicals and/or trialkylsiloxy radicals with 3 to 12 carbon atoms and E is H or

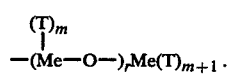

5. A process of preparing polymers of claim 4 wherein the polyamide of claim 1 is reacted with metal compounds of the formula

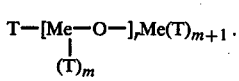

6. A process according to claim 5 wherein the reaction occurs in homogeneous solution in aprotic solvents at temperatures between 20° C. and 60° C., such that the molar ratio of the polyamide to the metal compound is between 1:0.5 and 1:1, and using concentrations of polyamide and metal compound in solution which are between 0.001% and 30% by weight.

7. A process according to claim 5 wherein T corresponds to anions of inorganic mineral acids, anions of organic carboxylic acids and/or complex forming agents and the reaction is a two phase reaction between the polyamide in an aprotic solvent, and the metal compound in a polar protic solvent, at temperatures between 20° C. and 220° C., such that the molar ratio of polyamide to metal compound is between 1:0.5 and 1:1 and in concentrations of 1–30% by weight of polyamide and 0.001–30% by weight of metal compound.

8. The polyamides of claim 1 wherein Z is selected from the group consisting of

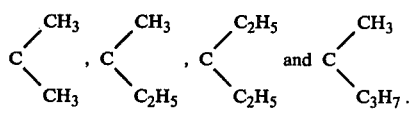

9. The polyamides of claim 1 wherein Z is

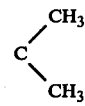

and $R^1$ and $R^2$ are hydrogen.

10. The polyamide of claim 4 wherein $R^1$ and $R^2$ are chlorine or bromine.

11. The polyamide of claim 4 wherein Z is selected from the group consisting of

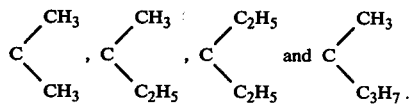

12. The polyamide of claim 4 wherein Z is

and $R^1$ and $R^2$ are hydrogen.

13. The polyamide of claim 4 wherein Me is selected from the group consisting of Sc to Zn, Y to Cd, La to Hg, Ac to U, Al, Pb and Bi.

14. the polyamide of claim 4 wherein T is the anion of an inorganic acid selected from the group consisting of HCl, $H_2SO_4$, $H_3PO_4$ and $HNO_3$.

15. The polyamide of claim 4 wherein T is the anion of a saturated aliphatic carboxylic acid having 1 to 18 carbon atoms.

16. The polyamide of claim 4 wherein T corresponds to the anion of a member selected from the group consisting of HCOOH, $(COOH)_2$, $CH_3COOH$ and $CH_3(CH_2)_{16}COOH$.

17. The polyamide of claim 4 wherein T is a complex forming agent selected from the group consisting of aliphatic diketones, ethylenediaminetetracetic acid, nitrilotriacetic acid and cyclopentadiene.

* * * * *